(12) United States Patent
Singh et al.

(10) Patent No.: US 8,212,026 B2
(45) Date of Patent: Jul. 3, 2012

(54) PROCESS FOR THE PREPARATION OF IVABRADINE HYDROCHLORIDE AND POLYMORPH THEREOF

(75) Inventors: Satyendra Pal Singh, Chandigarh (IN); Gajendra Singh, Chandigarh (IN); Lalit Wadhwa, Mohali (IN)

(73) Assignee: Ind-Swift Laboratories Limited, Chandigarh, IN (US)

( * ) Notice: Subject to any disclaimer, the term of this patent is extended or adjusted under 35 U.S.C. 154(b) by 270 days.

(21) Appl. No.: 12/602,348

(22) PCT Filed: May 29, 2008

(86) PCT No.: PCT/IN2008/000341
§ 371 (c)(1),
(2), (4) Date: Nov. 30, 2009

(87) PCT Pub. No.: WO2008/146308
PCT Pub. Date: Dec. 4, 2008

(65) Prior Publication Data
US 2010/0179316 A1    Jul. 15, 2010

(30) Foreign Application Priority Data

May 30, 2007 (IN) ............................ 1157/DEL/2007
Sep. 13, 2007 (IN) ............................ 1950/DEL/2007

(51) Int. Cl.
*C07D 223/16* (2006.01)
(52) U.S. Cl. ........................................................ 540/523
(58) Field of Classification Search .................... 540/523
See application file for complete search history.

(56) References Cited

U.S. PATENT DOCUMENTS

| | | | |
|---|---|---|---|
| 5,296,482 A | 3/1994 | Peglion et al. | |
| 5,296,596 A1 | 3/2004 | Peglion et al. | |
| 6,982,350 B2 | 1/2006 | Lerestif et al. | |
| 7,064,200 B2 | 6/2006 | Lerestif et al. | |
| 7,074,920 B2 | 7/2006 | Lerestif et al. | |
| 7,176,197 B2 | 2/2007 | Lerestif et al. | |
| 7,358,240 B2 | 4/2008 | Horvath et al. | |
| 7,361,649 B2 | 4/2008 | Horvath et al. | |
| 7,361,650 B2 | 4/2008 | Horvath et al. | |
| 7,361,651 B2 | 4/2008 | Horvath et al. | |
| 7,361,652 B2 | 4/2008 | Horvath et al. | |
| 7,384,932 B2 | 6/2008 | Horvath et al. | |
| 7,867,994 B2 | 1/2011 | Lerestif et al. | |
| 2008/0153803 A1 | 6/2008 | Horvath et al. | |
| 2008/0153804 A1 | 6/2008 | Horvath et al. | |
| 2008/0161284 A1 | 7/2008 | Horvath et al. | |
| 2008/0161285 A1 | 7/2008 | Horvath et al. | |
| 2008/0161286 A1 | 7/2008 | Horvath et al. | |
| 2008/0227771 A1 | 9/2008 | Horvath et al. | |
| 2009/0318416 A1 | 12/2009 | Horvath et al. | |
| 2009/0318417 A1 | 12/2009 | Horvath et al. | |
| 2009/0318418 A1 | 12/2009 | Horvath et al. | |
| 2009/0318419 A1 | 12/2009 | Horvath et al. | |
| 2009/0318420 A1 | 12/2009 | Horvath et al. | |
| 2009/0318682 A1 | 12/2009 | Lerestif et al. | |
| 2010/0016580 A1 | 1/2010 | Peglion et al. | |
| 2010/0041640 A1 | 2/2010 | Horvath et al. | |
| 2010/0056778 A1 | 3/2010 | Lerestif et al. | |
| 2010/0160628 A1 | 6/2010 | Peglion et al. | |
| 2010/0249397 A1 | 9/2010 | Peglion et al. | |
| 2010/0249398 A1 | 9/2010 | Peglion et al. | |

FOREIGN PATENT DOCUMENTS

| | | |
|---|---|---|
| WO | 2008/065681 A2 | 5/2008 |
| WO | 2008/125006 A1 | 10/2008 |
| WO | 2009124940 A1 | 10/2009 |
| WO | 2009153461 A2 | 12/2009 |
| WO | 2009158005 | 12/2009 |
| WO | 2010/023383 A1 | 3/2010 |
| WO | 2010/072409 A1 | 7/2010 |
| WO | 2010081342 | 7/2010 |
| WO | 2010089475 | 8/2010 |
| WO | 2011033194 | 3/2011 |

OTHER PUBLICATIONS

Konno et al., Physical and chemical changes of medicinals in mixtures with adsorbents in the solid state. IV.1) Study on reduced-pressure mixing for practical use of amorphous mixtures of flufenamic acid. Chem. Pharm Bull., 1990; 38 (7): 2003-2007.

*Primary Examiner* — Bruck Kifle
(74) *Attorney, Agent, or Firm* — Kramer & Amado, P.C.

(57) ABSTRACT

The present invention encompasses a process for the preparation of highly pure ivabradine hydrochloride by treating ivabradine with alcoholic hydrogen chloride. The invention further encompasses amorphous ivabradine hydrochloride and process for its preparation using suitable acid addition salts of ivabradine.

32 Claims, 2 Drawing Sheets

PROCESS FOR THE PREPARATION OF IVABRADINE HYDROCHLORIDE AND POLYMORPH THEREOF

FIELD OF THE INVENTION

The present invention relates to a novel process for the preparation of ivabradine hydrochloride, an useful antianginal agent. Further the present invention relates to novel amorphous form of ivabradine hydrochloride and process for the preparation thereof.

BACKGROUND OF THE INVENTION

Ivabradine hydrochloride of formula I, has very valuable pharmacological and therapeutic properties, and is useful in many cardiovascular diseases such as angina pectoris, myocardial infarct and associated rhythm disturbances and is chemically known as (S)-7,8-dimethoxy-3-{3-{N-[(4,5-dimethoxybenzocyclobut-1-yl)methyl]-N-(methyl)amino)propyl)-1,3,4,5-tetrahydro-2H-3-benzazepin-2-one.

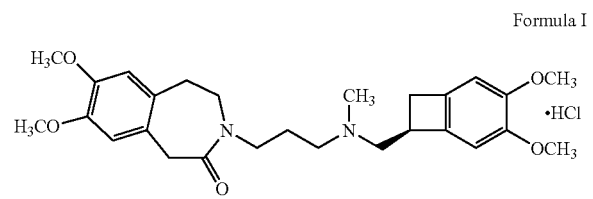

Formula I

Ivabradine hydrochloride is first disclosed in U.S. Pat. No. 5,296,482. The disclosed process comprises the condensation of (S)—N-[(4,5-dimethoxybenzocyclobut-1-yl)-methyl]-N-(methyl)amine of Formula II,

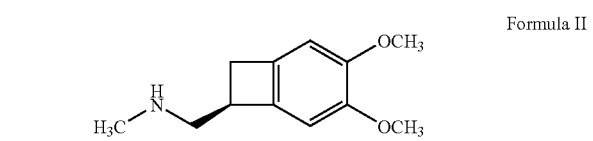

Formula II with 7,8-dimethoxy-3-[3-iodopropyl]-1,3-dihydro-2H-3-benzazepin-2-one Formula III,

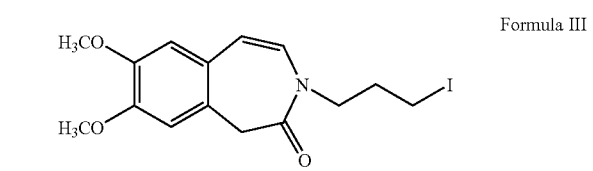

Formula III in acetone and in presence of a base such as potassium carbonate. The resulting benzazepine intermediate of formula IV is purified by column chromatography, and

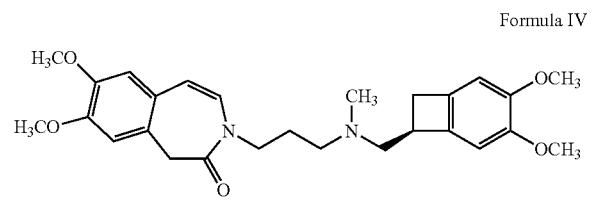

Formula IV is further reduced with palladium hydroxide in glacial acetic acid under the atmosphere of hydrogen gas to get ivabradine which is converted into its hydrochloride salt by the action of aqueous hydrochloric acid.

The methyl amine derivative of formula II is prepared by the reduction of 1-cyano-4,5-dimethoxybenzocyclobutane of Formula V,

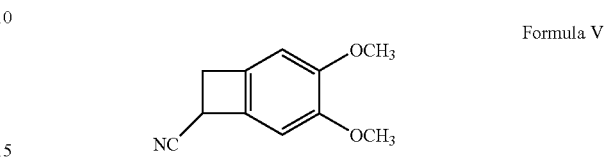

Formula V with borane tetrahydrofuran complex which upon condensation with ethyl chloroformate and further reduction with lithium aluminium hydride in tetrahydrofuran resulted in racemic compound of methyl amine derivative of formula II. The racemic compound is resolved to (+) isomer of methyl amine derivative of formula II with (d)-camphorsulphonic acid.

Benzazepine derivative of formula III is prepared by the reaction of sodium iodide with 7,8-dimethoxy-3-[3-chloropropyl]-1,3-dihydro-2H-3-benzazepin-2-one of formula VI,

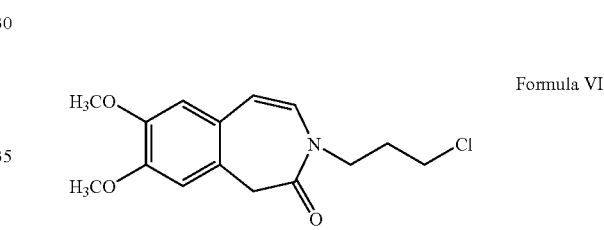

Formula VI in acetone and the resulting iodo intermediate is purified by dissolving it in water and extraction with dichloromethane.

It has been observed that the said process suffers from many drawbacks such as the use of borane-tetrahydrofuran complex which is unstable at room temperature and purification of intermediates and ivabradine by chromatographic techniques. The chromatographic technique for purification is cumbersome, tedious and difficult to utilize on an industrial scale.

The use of aqueous hydrochloride in the preparation of ivabradine hydrochloride is also not suggested because the removal of hydrochloric acid by distillation may lead to the decomposition and results in the generation of impurities and hence further purification is required. Also, use of highly flammable and large quantities of organic solvent in the preparation of benzazepine intermediate of formula IV makes this process unattractive for large scale production.

The above mentioned drawbacks call for an alternative and improved process for the preparation of highly pure ivabradine hydrochloride that would be commercially viable, reproducible on industrial scale and meets the needs of regulatory agencies.

Subsequent U.S. Pat. No. 7,176,197 reports α crystalline form of ivabradine hydrochloride. Several other crystalline forms such as beta, gamma, delta, beta-d, gamma-d and delta-d are also reported by Les Laboratories. There is no data available in the prior art for the existence of amorphous ivabradine hydrochloride.

Crystalline solids normally require a significant amount of energy for dissolution due to their highly organized, lattice like structures. For example, the energy required for a drug molecule to escape from a crystal is more than from an amorphous or a non-crystalline form. It is known that the amorphous forms in a number of drugs exhibit different dissolution characteristics and in some cases different bioavailability patterns compared to the crystalline form (Econno T., Chem. Phazm Bull., 1990; 38: 2003-2007). For some therapeutic indications, one bioavailability pattern may be favoured over another. An amorphous form of cefuroxime axietil is an example of one amorphous drug exhibiting much higher bioavailability than the crystalline forms, which leads to the selection of the amorphous form as the final drug substance for cefuroxime axietil pharmaceutical dosage form development. Additionally, the aqueous solubility of crystalline atorvastatin calcium is lower than its amorphous form, which may result in the difference in their in vivo bioavailability. Therefore, it is desirable to have amorphous forms of drugs with high purity to meet the needs of regulatory agencies and also highly reproducible processes for their preparation.

In view of the above, it is, therefore, desirable to provide an efficient, more economical, less hazardous and eco-friendly process for the preparation of highly pure ivabradine or a pharmaceutically acceptable salt thereof where impurity formation is less and hence avoids chromatographic purification and is convenient to operate on a commercial scale. Further, an amorphous form of ivabradine hydrochloride has also been provided in the present application for which the protection is sought.

SUMMARY OF THE INVENTION

One aspect of the present invention is to provide a process for the preparation of highly pure ivabradine hydrochloride of formula I which comprises:

a. condensing methylamine derivative of formula II

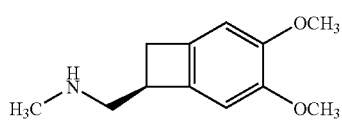

Formula II with 7,8-dimethoxy-3-[3-iodopropyl]-1,3-dihydro-2H-3-benzazepin-2-one of formula III

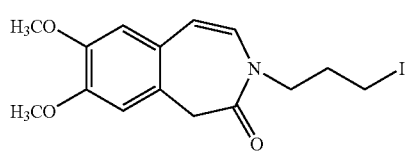

Formula III in a suitable polar solvent in the presence of a base to prepare benzazepine intermediate of formula IV;

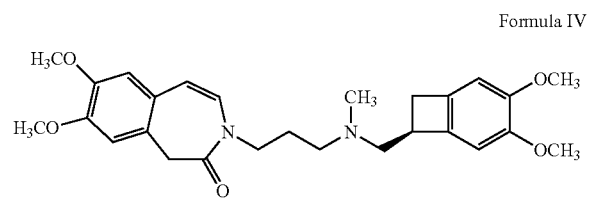

Formula IV b. reducing the compound of formula IV with palladium on carbon in glacial acetic acid under the atmosphere of hydrogen gas to get ivabradine; and
c. treating ivabradine in situ with alcoholic hydrogen chloride in a suitable solvent to prepare its hydrochloride salt.

Another aspect of the present invention is to provide a novel form of ivabradine hydrochloride i.e. amorphous ivabradine hydrochloride.

One another aspect of the present invention provides a process for the preparation of amorphous ivabradine hydrochloride which comprises:
a. hydrogenating the benzazepine intermediate of formula IV with palladium on carbon in glacial acetic acid under the atmosphere of hydrogen gas to get ivabradine;

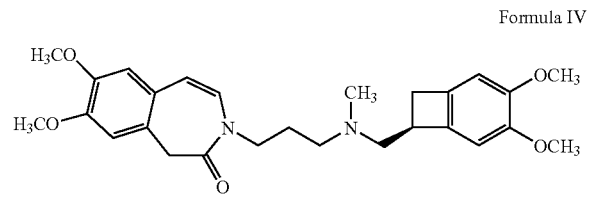

Formula IV b. treating ivabradine with a solution of organic acid in a suitable solvent to get ivabradine acid addition salt;
c. optionally purifying the ivabradine acid addition salt;
d. hydrolysing ivabradine acid addition salt with aqueous base in a suitable solvent; and
e. treating the resulting ivabradine in situ with alcoholic hydrogen chloride in organic solvent.

In other aspect there is provided a process for the preparation of highly pure ivabradine hydrochloride which comprises:
treating ivabradine with alcoholic hydrogen chloride in suitable solvent to prepare its hydrochloride salt.

One more another aspect of the present invention is to provide a process for the preparation of amorphous ivabradine hydrochloride which comprises:
treating ivabradine with a solution of organic acid in a suitable solvent to get ivabradine acid addition salt;
optionally purifying the ivabradine acid addition salt;
hydrolysing ivabradine acid addition salt with base in a suitable solvent; and
treating the resulting ivabradine with alcoholic hydrogen chloride in organic solvent.

Yet another aspect of the present invention is to provide a process for preparing amorphous ivabradine hydrochloride comprising:
a. treating ivabradine hydrochloride with base in a suitable solvent; and
b. treating the resulting ivabradine with alcoholic hydrogen chloride in organic solvent.

Still yet another aspect of the present invention is to provide a process for the preparation of amorphous ivabradine hydrochloride which comprises:

a. dissolving ivabradine hydrochloride in a mixture of lower alkanol and ketone at ambient temperature;
b. heating the solution to 40-50° C.;
c. distilling the solvent; and
d. isolating amorphous ivabradine hydrochloride.

In still yet another aspect of the present invention provides a process for preparing α crystalline form of ivabradine hydrochloride comprising the steps of:
a. heating a solution ivabradine hydrochloride in suitable solvent;
b. distilling off some of the solvent;
c. filtering the reaction mixture to obtain ivabradine hydrochloride; and
d. isolating α crystalline form of ivabradine hydrochloride.

Ivabradine acid addition salts prepared in the present invention also forms the inventive part of the invention. Ivabradine oxalate is isolated as crystalline solid and is another inventive part of the invention.

DETAILED DESCRIPTION OF THE INVENTION

Figure 1:
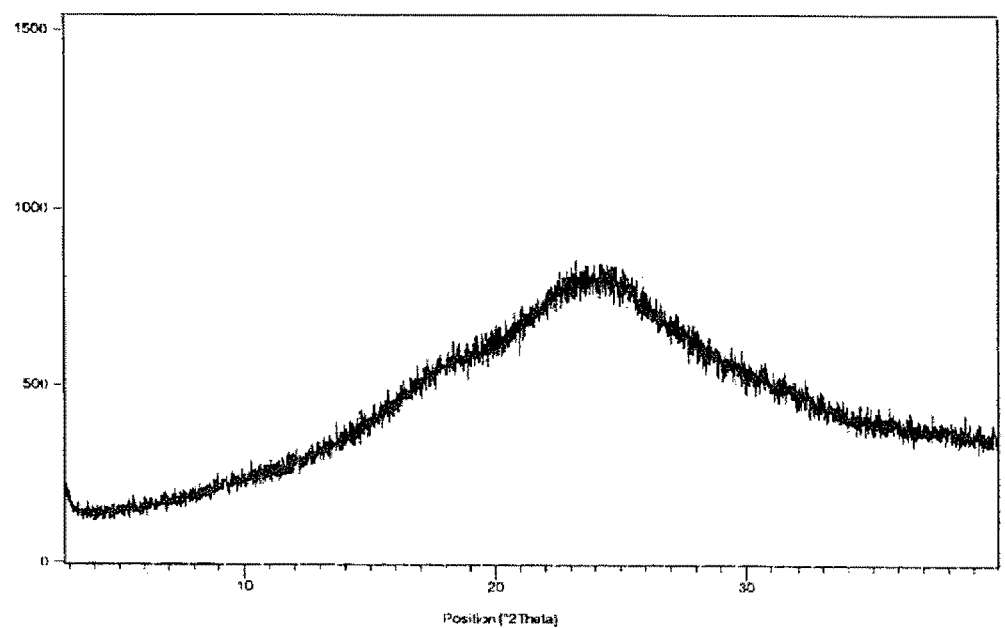
FIG. 1 is a powdered X-ray diffraction pattern for amorphous ivabradine hydrochloride.

The instant invention relates to an efficient and industrially advantageous process for the preparation of highly pure ivabradine or a pharmaceutically acceptable salt and in particular ivabradine hydrochloride.

One aspect of the present invention relates to an improved process for the preparation of highly pure ivabradine hydrochloride by initially condensing methylamine derivative of formula II with benzazepine derivative of formula III to form benzazepine intermediate of formula IV in the presence of a base, in a polar aprotic or protic solvents. The base can be selected from alkali metal carbonates, bicarbonates and hydroxides and preferably potassium carbonate. The polar aprotic or protic solvent is selected from tetrahydrofuran, acetone, acetonitrile, dimethylformamide, dimethylsulfoxide, water, isopropanol, $C_1$-$C_4$ linear aliphatic alcohols such as methanol, ethanol etc. and mixtures thereof. More preferably, the solvent is dimethylformamide or dimethylsulfoxide and most preferably the solvent is dimethylformamide. It is advantageous to use dimethylformamide during condensation reaction because reaction rate is faster and it takes only 2-3 hours for completion of reaction as compared to prior art processes wherein 18 hours are required in acetone. Reaction is conducted at 30-75° C. and preferably at 50-60° C. The completion of reaction is monitored by high performance liquid chromatography. After completion of the reaction, the reaction mass is cooled to ambient temperature and diluted with water. The product is extracted in organic solvent from aqueous layer and some impurities remain in the aqueous layer. The solvent can be selected from halogenated hydrocarbon such as methylene dichloride, ethylene dichloride, carbon tetrachloride, chloroform and aliphatic ester such as ethyl acetate and preferably methylene chloride is used. Thereafter, solvent is distilled off completely and the product is purified by acid base wash treatment. Specifically the residue is treated with hydrochloric acid in water and washed with solvent such as ethyl acetate, thereafter the aqueous layer is neutralized with base and the desired compound is extracted in organic solvent. The organic solvent can be selected from halogenated hydrocarbons and aliphatic esters as mentioned above and preferably ethyl acetate is used. The product is obtained in high purity and no chromatographic purification is required.

It has also been found that during condensation process an unknown impurity has also been formed, which is not easily removed by using the prior art isolation process and hence decreases the purity of the condensed product. But during the process of present invention, it is observed that the said unknown impurity can be easily removed by extracting the desired product from the reaction mixture with halogenated solvents such as methylene dichloride, ethylene dichloride, carbon tetrachloride, chloroform. This further avoids the use of tedious chromatographic purification.

According to another aspect of the present invention, benzazepine intermediate of formula IV is most preferably prepared by condensing methylamine derivative of formula II with 7,8-dimethoxy-3-[3-iodopropyl]-1,3-dihydro-2H-3-benzazepin-2-one of formula III in demineralized water and in the presence of a base. The condensation reaction is carried out at 45-60° C. preferably at 50-55° C. and it takes 10-20 hours for completion of reaction. The progress of reaction is monitored by high performance liquid chromatography (HPLC). The product is extracted in lower aliphatic ester solvent such as ethyl acetate. Ethyl acetate layer is further treated with aqueous acidic solution and the resulting layers are separated. The aqueous layer is treated with basic solution and the product is extracted in lower aliphatic ester solvent such as ethyl acetate. Ethyl acetate layer is removed by known methods such as evaporation, distillation with or without vacuum etc to get benzazepine intermediate of formula IV. The base is used in the condensation step can be selected from alkali metal carbonates, bicarbonates and hydroxides and preferably potassium carbonate.

The intermediates II and III can be prepared by the methods reported in the prior art with minor modifications. Specifically the methyl amine derivative of Formula II is prepared by the reduction of 1-cyano-4,5-dimethoxybenzocyclobutane of formula V

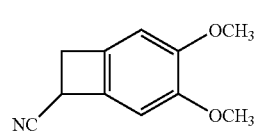

Formula V using reducing agent such as borane complexes like borane dimethyl sulfide complex in tetrahydrofuran which is converted to acid addition salt by treatment with acid in suitable solvent. Particularly hydrochloride salt is prepared by treating the amino derivative with alcoholic hydrogen chloride; ethereal hydrogen chloride such as ethanol hydrogen chloride, isopropyl acetate hydrogen chloride, isopropyl ether hydrogen chloride etc.

Hydrochloric acid salt of the obtained amino intermediate is further condensed with ethyl chloroformate in the presence of a suitable base to prepare the corresponding amide. The resulting amide is reduced with lithium aluminium hydride in tetrahydrofuran to prepare racemic methyl amine intermediate of formula II. Racemic intermediate is further resolved with suitable resolving agent such as (d)-camphorsulphonic acid to produce desired (+) isomer methyl amine of formula II which can optionally be used in oily form or can be isolated.

The said process is very useful during its application at large-scale production because borane dimethyl sulphide complex is stable at room temperature hence its storage and handing is not difficult during large scale production.

Specifically the benzazepine compound of formula III is prepared by the reaction of 7,8-dimethoxy-3-[3-chloropropyl]-1,3-dihydro-2H-3-benzazepin-2-one of formula VI with sodium iodide in acetone followed by its purification by slurry washing of the residue with acetone.

The intermediates of formula V and VI are prepared by the methods reported in the literatures (T. Kametani et al, Tetrahedron 1973; vol. 29; pages 73-76 and Reiffer M. et al., J. Med. Chem. 1990; vol 33 (5): 1496-1504).

The intermediate of formula V can also be prepared by the reaction of 6-bromovaretraldehyde with cyanoacetic acid in the presence of ammonium acetate and in solvents optionally selected from pyridine, toluene, benzene etc. or mixtures thereof. The isolated intermediate is further reduced with sodium borohydride in the presence of aqueous base. Generally bases are selected from sodium bicarbonate, sodium carbonate, potassium hydroxide, sodium hydroxide or mixtures thereof to get β-(2-bromo-4,5-dimethoxyphenyl)-α-cyanopropionic acid. The resulting acid upon decarboxylation in N,N-dimethyl acetamide and subsequent reaction with sodium amide or potassium amide in liquid ammonia is converted to 1-cyano-4,5-dimethoxybenzocyclobutane of formula V.

Furthermore, the intermediate of formula VI can also be prepared by the halogenation of 3,4-dimethoxyphenyl acetic acid with some halogenating agents such as thionyl chloride in chlorinated solvents such as methylene dichloride. The obtained chloro compound is further condensed with aminoacetaldehyde dimethyl acetal in the presence of a suitable base to prepare corresponding amide derivative. The ring closure of resulting amide into benzazepin moiety is carried out in presence of an acid, for example, hydrochloric acid, glacial acetic acid or mixtures thereof. Obtained benzazepin moiety is further alkylated with 1-bromo-3-chloro-propane in presence of a suitable base such as potassium tertiary butoxide in an organic solvent to obtain 7,8-dimethoxy-3-[3-chloropropyl]-1,3-dihydro-2H-3-benzazepin-2-one of formula VI. The organic solvents can be selected from acetone, dimethylsulfoxide, dimethylformamide, etc. or mixtures thereof.

Benzazepine intermediate of formula IV prepared by the processes of present invention is hydrogenated and converted into highly pure ivabradine or a pharmaceutically acceptable salt thereof.

Typically, the condensed product i.e. (S)-7,8-dimethoxy-3-{3{N-[(4,5-dimethoxybenzocyclobut-1-yl)methyl]-N-(methyl)amino)propyl)-1,3-dihydro-2H-3-benzazepin-2-one of formula IV is converted to ivabradine hydrochloride. The compound of formula IV is catalytically hydrogenated using palladium on carbon catalyst in acetic acid under hydrogen pressure of 1-7 kg/cm². The hydrogenation reaction is conducted at ambient temperature and it takes 4-10 hours for completion of reaction, which is monitored by high performance liquid chromatography (HPLC). The catalyst is filtered out and the product is extracted in organic solvent from filtrate or acetic acid is removed by distillation from the filtrate. The organic solvent consists of methylene dichloride, ethylene dichloride, carbon tetrachloride, chloroform. The filtrate is further treated with dilute hydrochloric acid and extracted with same organic solvent.

Thereafter the combined extracts were distilled and the resulting residue is treated with dilute hydrochloric acid. The aqueous layer is washed with organic solvent such as ethyl acetate to remove impurities and neutralized with base like aqueous sodium hydroxide. Thereafter the desired compound is extracted in organic solvent. The organic solvent can be selected from above mentioned solvents such as halogenated hydrocarbon and aliphatic esters and preferably ethyl acetate is used. Optionally the ivabradine is isolated; otherwise organic layer itself is treated with alcoholic hydrogen chloride to prepare highly pure ivabradine hydrochloride. It is advantageous to dry the organic layer using drying agent such as sodium sulfate or the like before adding alcoholic hydrogen chloride.

Preferably, ivabradine of formula I is converted into pharmaceutically acceptable acid addition salts using alcoholic acid mixture. Particularly the hydrochloride salt preparation is carried out using alcoholic hydrogen chloride. In general, a solution of alcoholic hydrogen chloride is prepared by purging dry hydrogen chloride in alcohol by following the methods reported in prior art. The percentage of hydrogen chloride in alcohol is preferably selected between 10-25%. The alcohol used in the solution of alcohol-hydrogen chloride is selected from $C_1$-$C_4$ branched or linear aliphatic alcohols and more preferably the solvent is methanol, ethanol, n-butanol or isopropanol and most preferably the solvent is methanol and isopropanol. The precipitated ivabradine hydrochloride is isolated in high yield and purity of greater than 99.0% area by HPLC. XRD pattern shows that material is amorphous in nature, substantially as depicted in FIG. 1.

Amorphous Ivabradine hydrochloride is novel and forms one aspect of the present invention. Amorphous ivabradine hydrochloride is further characterized by a differential scanning calorimetry ("DSC") thermogram, which shows one endothermic peak around 194° C. due to melting.

Another aspect of the present invention relates to the preparation of highly pure amorphous ivabradine hydrochloride from ivabradine through ivabradine acid addition salts. Specifically the ivabradine is treated with a solution of organic acid in solvent selected from lower aliphatic ketone such as acetone; ester such as ethyl acetate and nitrile such as acetonitrile to prepare ivabradine acid addition salt.

The organic acid can be selected from acetic acid, propionic acid, maleic acid, fumaric acid, tartaric acid, oxalic acid, citric acid, benzoic acid, methanesulphonic acid, isethionic acid, benzenesulphonic acid, toluenesulphonic acid and the like. Preferably the acid is selected from oxalic acid, citric acid, methanesulphonic acid, benzenesulphonic acid, toluenesulphonic acid and most preferably the acid is oxalic acid.

Particularly the ivabradine oxalate is prepared by treating ivabradine with oxalic acid in acetone and reaction mass is stirred at ambient temperature for sufficient tine to prepare the oxalate salt. The oxalate salt is isolated by filtration and optionally recrystallized in acetonitrile to isolate pure ivabradine oxalate. The ivabradine oxalate is isolated as crystalline solid and may be characterized by at least one of Karl Fisher or TGA, X-Ray power diffraction (XRD), or differential scan calorimetry (DSC).

Figure 3:
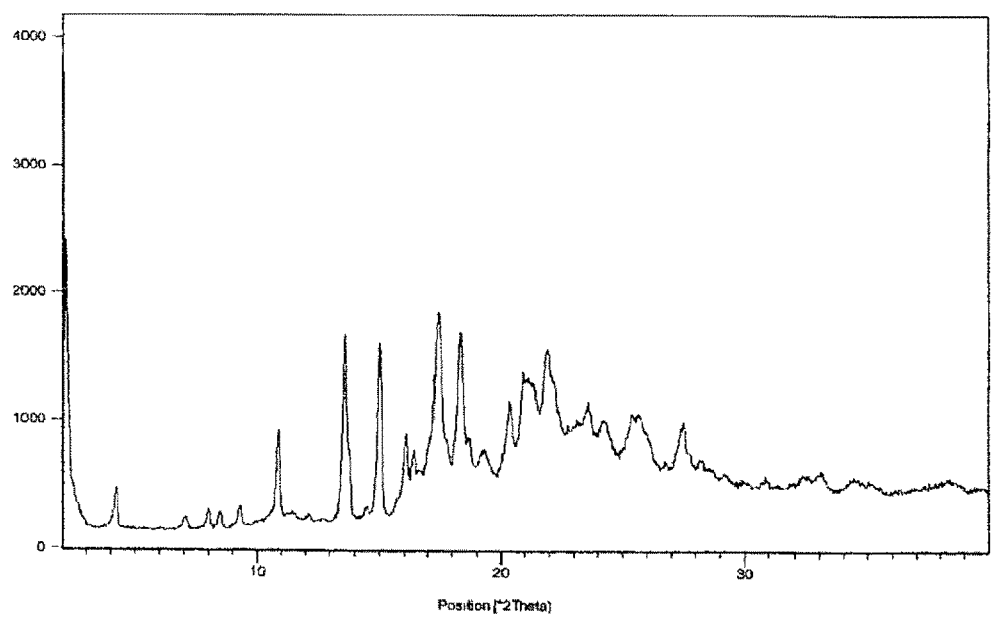
FIG. 3 is a powdered X-ray diffraction pattern for ivabradine oxalate.

Crystalline ivabradine oxalate is characterized by powdered X-ray diffraction patterns having peaks at about 2.04, 2.13, 4.26, 7.06, 8.02, 8.53, 9.32, 10.91, 13.63, 15.07, 16.11, 16.44, 17.48, 18.37, 19.32, 20.38, 20.94, 21.95, 23.61, 24.26, 27.54 and 33.07 degrees two theta, substantially as depicted in FIG. 3.

Figure 4:
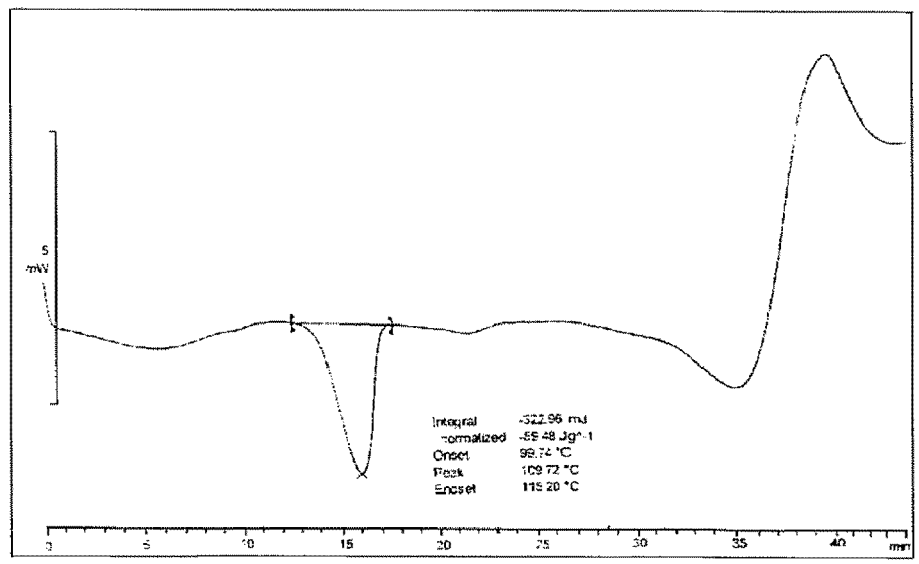
FIG. 4 is a DSC thermogram for ivabradine oxalate.

Crystalline ivabradine oxalate is further characterized by a differential scanning calorimetry ("DSC") thermogram, which shows one endothermic peak around 110° C. due to melting, substantially as depicted in FIG. 4.

X-ray diffraction of amorphous ivabradine hydrochloride and crystalline ivabradine oxalate are measured on a PANalytical X'Pert Pro diffractometer with Cu radiation and expressed in terms of two-theta, d-spacings and relative intensities. One of the ordinary skills in the art understands that experimental differences may arise due to differences in instrumentation, sample preparation or other factors. DSC analysis was performed using a Mettler Toledo 822 Star$^e$. The crucible was crimped and punched prior to analysis. The weight of the samples was about 4-6 mg; the samples were scanned at a rate of 5° C./min from 30° C. to 250° C. The oven was constantly purged with nitrogen gas at a flow rate of 80 ml/min. Standard 40 μl aluminum crucibles covered by lids with one hole were used.

It is advantageous to purify the acid addition salt of ivabradine by known methods such as crystallization or slurring in suitable solvent to remove the unwanted impurities. Preferably, the isolated acid addition salt of ivabradine is recrystallized in a suitable organic solvent such as acetonitrile Acid addition salt of ivabradine is hydrolyzed with a suitable base in demineralized water to get ivabradine. The base can be selected from sodium hydroxide, potassium hydroxide, sodium carbonate, potassium carbonate, sodium bicarbonate and potassium bicarbonate and preferably sodium hydroxide is used. After complete hydrolysis, the desired compound is extracted in organic solvent. The organic solvent can be selected from halogenated hydrocarbon and aliphatic esters and preferably ethyl acetate is used. Ethyl acetate is distilled out to isolate the ivabradine as oil. Crude ivabradine is further dissolved in a suitable organic solvent such as acetone, ethyl acetate preferably in acetone. The pH of the resulting clear solution is adjusted to 1.0 to 2.0 with alcoholic hydrogen chloride and stirred for 30 to 60 minutes to get highly pure amorphous ivabradine hydrochloride. It is advantageous to dry the organic layer using drying agent such as sodium sulfate or the like before adding alcoholic hydrogen chloride.

Amorphous ivabradine hydrochloride is isolated by removing the solvent from the reaction mixture by known methods such as evaporation, distillation with or without vacuum etc.

Optionally the amorphous ivabradine hydrochloride is further stirred for 30 to 60 minutes in a suitable organic solvent such as n-heptane, n-hexane and cyclohexane then filtered and washed with same organic solvent to get highly pure amorphous ivabradine hydrochloride.

In yet another aspect of the present invention is provided a process for the preparation of amorphous ivabradine hydrochloride by dissolving ivabradine hydrochloride in a mixture of lower alkanol and ketone at ambient temperature and further heated to 40-50° C., distilling out the solvent under vacuum, isolating amorphous ivabradine hydrochloride.

The lower alkanol can be selected from methanol, ethanol, propanol, isopropanol and preferably methanol is used. The ketone can be selected from acetone, methyl ethyl ketone, methyl isobutyl ketone and preferably acetone is used. Mixture of lower alkanol and ketone is used in a ratio of 1:2-6 (v/v) more preferably 1:3 (v/v) and most preferably 1:2 (v/v). Specifically ivabradine hydrochloride is dissolved in a mixture of methanol and acetone by simple stirring at room temperature without using prior heating. Amorphous ivabradine hydrochloride is isolated by removing the solvent from the reaction mixture by known methods such as evaporation, distillation with or without vacuum etc. Alternatively the isolation of highly pure amorphous ivabradine hydrochloride is carried out by stirring the amorphous ivabradine hydrochloride in a suitable organic solvent such as n-heptane, n-hexane and cyclohexane for about 30 to 60 minutes followed by filtering and washing with same organic solvent to get highly pure amorphous ivabradine hydrochloride.

In yet another aspect of the present invention amorphous ivabradine hydrochloride can also be prepared from α crystalline form of ivabradine hydrochloride. Specifically the crystalline ivabradine hydrochloride is treated with suitable base and in a suitable solvent followed by regeneration of ivabradine hydrochloride from the solution of isopropyl alcohol/hydrogen chloride to get amorphous ivabradine hydrochloride. The base can be selected from sodium hydroxide, potassium hydroxide, sodium carbonate, potassium carbonate, sodium bicarbonate and potassium bicarbonate. The solvent can be selected from ethyl acetate, isopropyl acetate, methyl isobutyl ketone and acetone.

In still yet another aspect of the present invention the α crystalline form of ivabradine hydrochloride can also be prepared by recrystallization of ivabradine hydrochloride in suitable organic solvent such as acetonitrile, followed by addition of lower aliphatic ketone, ester, straight branched or cyclic ethers or mixtures thereof heat the mixture, removed solvents and recovered the α crystalline form of ivabradine hydrochloride.

In still yet another aspect of the present invention the α crystalline form of ivabradine hydrochloride can also be prepared from amorphous ivabradine in suitable organic solvent such as lower aliphatic ketone, ester, straight branched or cyclic ethers or nitriles or mixtures thereof. The lower aliphatic ketonic solvents can be selected from methyl isobutyl ketone, acetone or the like. The esters can be selected from ethyl acetate and isopropyl acetate. The ether can be selected from isopropyl ether, tetrahydrofuran and the like. The nitrile can be acetonitrile and the like. Ivabradine hydrochloride is taken in suitable solvent and heated at 60-90° C. for sufficient time to transform to α crystalline form of ivabradine hydrochloride.

Having described the invention with reference to certain preferred embodiments, other embodiments will become apparent to one skilled in the art from consideration of the specification. The invention is further defined by reference to the following examples describing in detail the preparation of the product and methods of use of the invention. It will be apparent to those skilled in the art that many modifications, both to materials and methods, may be practiced without departing from the scope of the invention.

EXAMPLES

Example 1

Preparation of Ivabradine Hydrochloride

Step 1: Preparation of (S)-7,8-dimethoxy-3-{3-{N-[(4,5-dimethoxybenzocyclobut-1-yl)methyl]-N-(methyl)amino)propyl)-1,3-dihydro-2H-3-benzazepin-2-one To a mixture of (S)—N-[(4,5-dimethoxybenzocyclobut-1-yl)-methyl]-N-(methyl)amine (42 g) and N,N-dimethylformamide (220 ml) was charged 7,8-dimethoxy-3-[3-iodopropyl]-1,3-dihydro-2H-3-benzazepin-2-one (75 g) and potassium carbonate (42 g) at room temperature. The reaction mixture was heated and stirred the reaction mass at 50-55° C. for 2 hours and the completion of reaction was monitored by HPLC/TLC. After completion of reaction, reaction mass was cooled to 25-30° C. and diluted with dimineralized water (1000 ml). The reaction mixture was extracted with methylene dichloride (400 ml×200 ml) and the layers were separated. Methylene chloride was distilled off completely. To the residue, dimineralized water (200 ml) and hydrochloric acid (50 ml) were added and the aqueous solution is washed with ethyl acetate (200 ml×3). The layers were separated and to the aqueous layer 50% (w/v) sodium hydroxide solution (120 ml) was added at 25-30° C. The aqueous layer was extracted with ethyl acetate (400 ml+200 ml) and the combined ethyl acetate layer was washed with 5% (w/v) sodium hydroxide solution (300 ml). Ethyl acetate layer was dried over anhydrous sodium sulfate and then ethyl acetate was distilled out completely under vacuum to get the title compound.

Step 2: Preparation of (S)-7,8-dimethoxy-3-{3-[N-[(4,5-dimethoxybenzocyclobut-1-yl)methyl]-N-(methyl)amino) propyl)-1,3,4,5-tetrahydro-2H-3-benzazepin-2-one hydrochloride Benzazepine compound (85 g) obtained in step 1 was taken in acetic acid (700 ml), and was hydrogenated under a hydrogen pressure (1-2 kg) at room temperature in the presence of Pd/C (10%, 70 g). Further hydrogenation was continued with 6-7 kg/cm$^2$ hydrogen gas pressure at 20° C. for 6-8 hours. After completion of hydrogenation (monitored by HPLC), the catalyst was filtered off and catalyst was washed with water (800 ml). The filtrate was then extracted with methylene chloride (700 ml) and to the aqueous layer hydrochloric acid solution (50 ml) was added. The aqueous layer was again extracted with methylene dichloride (300 ml×3). The combined organic layer was distilled off and to the residue demineralized water (400 ml) and hydrochloric acid solution (90 ml) were charged followed by ethyl acetate (400 ml). The reaction mixture was stirred at 30-35° C. for half an hour and the layers were separated. The aqueous layer was again washed with ethyl acetate (500 ml). Thereafter aqueous layer was treated with 50% (w/v) sodium hydroxide solution (150 ml). The aqueous layer was extracted with ethyl acetate (400 ml+250 ml) and combined ethyl acetate layer was washed with 5% (w/v) sodium hydroxide solution (400 ml). Ethyl acetate layer was dried over anhydrous sodium sulfate and then solvent was distilled out completely. The residue was taken in ethyl acetate (400 ml) and to this isopropyl alcohol-hydrogen chloride (50 ml) was added slowly and was stirred for 4-5 hours. The product obtained was filtered, washed with ethyl acetate (85 ml) and dried at 55-60° C. to obtain the title compound in amorphous form having purity 98.5% area by HPLC.

Example 2

Preparation of Benzazepine Intermediate of Formula IV 7,8-Dimethoxy-3-[3-iodopropyl]-1,3-dihydro-2H-3-benzazepin-2-one (38 g) and potassium carbonate (60 g) were added to a mixture of (S)—N-[(4,5-dimethoxybenzocyclobut-1-yl)-methyl]-N-(methyl)amine (20 g) and demineralized water (100 ml) at room temperature. The reaction mixture was heated and stirred at 50-55° C. for 12-16 hours. After completion of reaction, reaction mass was cooled to 25-30° C. and the product is extracted in ethyl acetate (100 ml). The aqueous layer was further extracted with ethyl acetate (60 ml). Combined ethyl acetate layers was acidified with aqueous hydrochloric acid and stirred. The layers were separated and pH of the aqueous layer was adjusted to 10.5-12.5 with aqueous sodium hydroxide solution. The aqueous layer is extracted with ethyl acetate (140 ml+60 ml). Ethyl acetate was distilled out completely under vacuum to get the title compound.

Example 3

Preparation of Amorphous Ivabradine Hydrochloride

Benzazepine intermediate of formula IV (85 g) was taken in acetic acid (700 ml), and was hydrogenated under a hydrogen pressure (1-2 kg) at room temperature in the presence of Pd/C (10%, 70 g). Further hydrogenation was continued with 6-7 kg/cm$^2$ hydrogen gas pressure at 20° C. for 6-8 hours. After completion of hydrogenation (monitored by HPLC), the catalyst was filtered off and acetic acid was removed by distillation. To the residue demineralized water (360 ml) and hydrochloric acid (40 ml) were added followed by addition of ethyl acetate (200 ml). The resulting mixture was stirred and the layers were separated. The aqueous layer was washed with ethyl acetate (100 ml). The pH of the aqueous layer was adjusted to 10.5-12.5 with aqueous sodium hydroxide solution and product was extracted in ethyl acetate (400 ml). Ethyl acetate layer was dried over anhydrous sodium sulfate and then solvent was distilled out completely. The residue was taken in ethyl acetate (1020 ml) and to this oxalic acid (34 g) in acetone (68 ml) was added slowly and was stirred for 3-4 hours at ambient temperature. The ivabradine oxalate obtained was filtered and recrystallized in acetonitrile. Ivabradine oxalate was taken in demineralized water (340 ml) and pH of the reaction mixture was adjusted to 10-12 with aqueous sodium hydroxide solution and stirred. The resulting mixture is then extracted with ethyl acetate (340 ml). Ethyl acetate was distilled out completely. Thereafter, the residue was taken in acetone (220 ml) and to this methanol-hydrogen chloride (30-35 ml) was added slowly and was stirred for 30 minutes. The solvent was removed by distillation under reduced pressure. The amorphous product, thus obtained, was further stirred with n-heptane for 30-40 minutes, filtered, washed with n-heptane (50 ml) and dried at 40-45° C. to obtain amorphous ivabradine hydrochloride having purity 99.9% area by High performance liquid chromatography (HPLC). XRD pattern showed that product was amorphous in nature and same as depicted in FIG. 1.

Example 4

Preparation of Amorphous Ivabradine Hydrochloride

Step-1: Preparation of Ivabradine Oxalate

Figure 2:
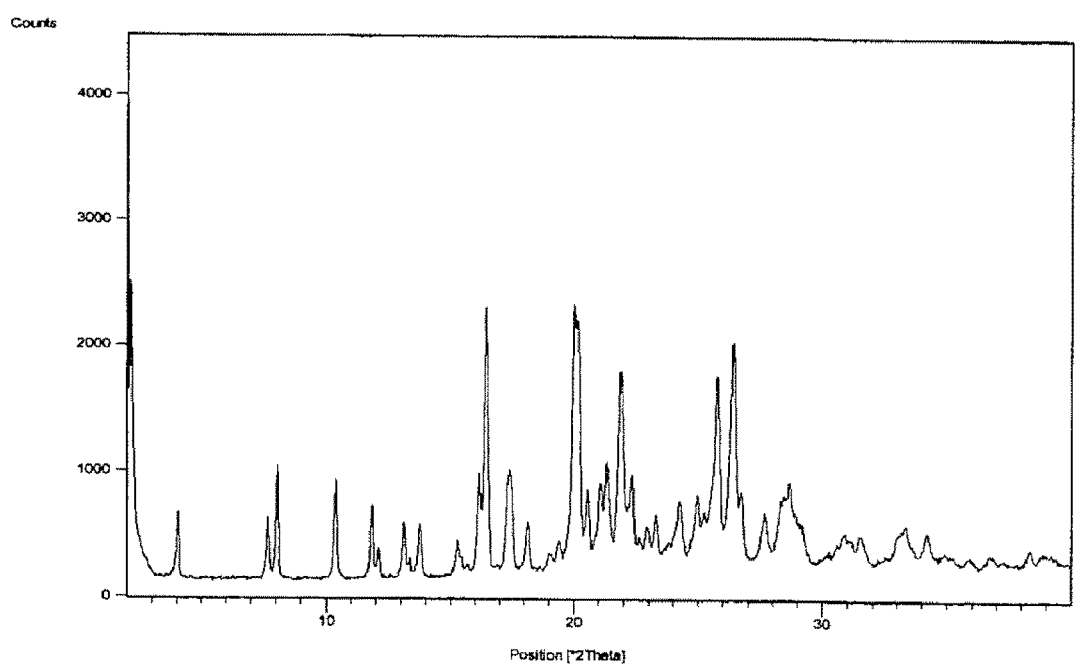
FIG. 2 is a powdered X-ray diffraction pattern for α crystalline form of ivabradine hydrochloride.

Ivabradine (44 g) was dissolved in ethyl acetate (700 ml) and to this oxalic acid (22 g) in acetone (50 ml) was added slowly and stirred for 3-4 hours at ambient temperature. The ivabradine oxalate, thus obtained was filtered, washed with ethyl acetate (100 ml) and recrystallized in acetonitrile (350 ml). XRD pattern shows that isolated ivabradine oxalate was crystalline in nature and depicted in FIG. 2.

Step-2: Preparation of Amorphous Ivabradine Hydrochloride

Ivabradine oxalate was taken in demineralized water (200 ml) and to this aqueous sodium hydroxide solution (100 ml) was added and stirred. The resulting mixture was extracted with ethyl acetate (250 ml). Ethyl acetate layer was dried over anhydrous sodium sulfate and then solvent was distilled out completely. The resulting residue was taken in acetone (100 ml) and to this methanol-hydrogen chloride (7 ml) was added slowly and was stirred for 30 minutes. Thereafter the solvent was removed by distillation under reduced pressure. To the amorphous product, n-heptane (100 ml) was added and stirred for 30 minutes, filtered, washed with n-heptane (50 ml) and dried at 40-45° C. to obtain the title compound.

Example 5

Preparation of Amorphous Ivabradine Hydrochloride

Ivabradine hydrochloride (20 g) was dissolved in stirred mixture of acetone (100 ml) and methanol (50 ml) at ambient temperature. The solution was heated to 50° C. and the solvent was distilled off under reduced pressure. The amorphous product, thus obtained, was stirred with n-heptane (100 ml). The reaction mixture was filtered, washed with n-heptane and dried at 40-45° C. under vacuum to obtain the title compound.

Example 6

Preparation of Amorphous Ivabradine Hydrochloride

α-Crystalline form of ivabradine hydrochloride (6 gm) was taken in water (30 ml) and basified by sodium hydroxide solution (50%). Ivabradine, thus formed, was extracted with ethyl acetate (50 ml) and was dried over anhydrous sodium sulfate. Solvent was distilled off. Residue was taken in ethyl acetate (30 ml) and isopropyl alcohol hydrogen chloride (5 ml) was added slowly and was stirred for 2 hours. Product thus obtained was filtered, washed with ethyl acetate (6 ml) and dried at 55-60° C. to obtained amorphous ivabradine hydrochloride having purity 99.93% area by HPLC.

Example 7

Preparation of α Crystalline Form of Ivabradine Hydrochloride

Ivabradine hydrochloride (47 g) was taken in acetonitrile (940 ml) and heated to 80±2° C. for 30 minutes till clear solution. Thereafter, half of the acetonitrile was distilled off and the reaction mass was cooled, filtered and washed with acetonitrile to get wet cake of the product.

Obtained wet cake was further dissolved in ethyl acetate (611 ml) at room temperature then heated the mixture to 75-80° C. and maintained for 60 minutes. The reaction mixture was concentrated by distillation of about one third of ethyl acetate. The reaction mass was cooled, filtered, washed with ethyl acetate and dried under vacuum to obtain the title compound.

Example 8

Preparation of α Crystalline Form of Ivabradine Hydrochloride from Amorphous Form Amorphous ivabradine hydrochloride (4 gm) was taken in ethyl acetate (60 ml) and heated to reflux for 30 minutes. Thereafter one third of ethyl acetate was distilled off and the reaction mass was cooled to 25-30° C. The product obtained was filtered and dried to obtain the title compound having purity 99.89% area by HPLC.

Example 9

Preparation of α Crystalline Form of Ivabradine Hydrochloride

Ivabradine hydrochloride (2 gm) was taken in acetone (200 ml) and heated to reflux till clear solution, suspended material was filtered off. Thereafter 60% of acetone was distilled off and reaction mass was cooled to room temperature. The product was filtered, washed with acetone (10 ml) and dried to obtain the title compound having purity 99.73% area by HPLC.

We claim:

1. A process for the preparation of highly pure amorphous ivabradine hydrochloride of formula I,

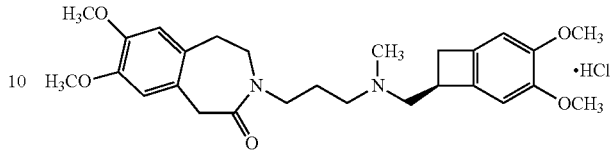

Formula I comprising the steps of:
a. condensing methylamine of formula II,

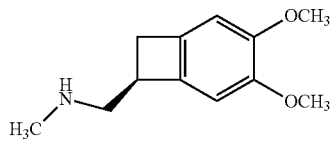

Formula II with 7,8-dimethoxy-3-[3-iodopropyl]-1,3-dihydro-2H-3-benzazepin-2-one of formula III

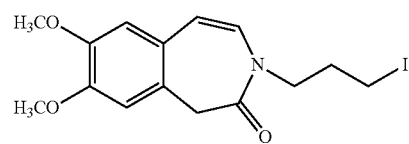

Formula III in the presence of a base in polar solvent to prepare benzazepine intermediate of formula IV;

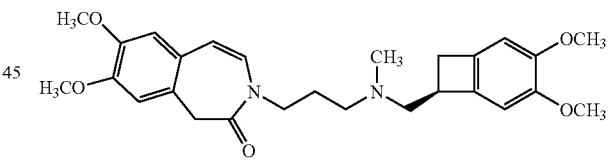

Formula IV b. hydrogenating the benzazepine intermediate of formula IV with palladium on carbon in glacial acetic acid under an atmosphere of hydrogen to get ivabradine,
c. converting ivabradine in situ to its hydrochloride salt using alcoholic hydrogen chloride in an organic solvent; and
d. isolating amorphous ivabradine hydrochloride.

2. The process according to claim 1, wherein in step a), said base is selected from the group consisting of alkali metal carbonates, bicarbonates and hydroxides.

3. The process according to claim 1, wherein in step a), said base is potassium carbonate.

4. The process according to claim 1, wherein in step a), said polar solvent is selected from the group consisting of water, tetrahydrofuran, acetone, acetonitrile, dimethylformamide, dimethylsulfoxide, isopropanol, and $C_1$-$C_4$ linear aliphatic alcohols.

5. The process according to claim 1, wherein in step c), said alcoholic hydrogen chloride contains an alcohol selected from the group consisting of $C_1$-$C_4$ branched or linear aliphatic alcohols.

6. The process according to claim 1, wherein in step c, the said organic solvent is selected from the group consisting of halogenated hydrocarbons and aliphatic esters.

7. A process for the preparation of amorphous ivabradine hydrochloride comprising the steps of:
 a. hydrogenating a benzazepine intermediate of formula IV with palladium on carbon in glacial acetic acid under the atmosphere of hydrogen gas to form ivabradine;

Formula IV

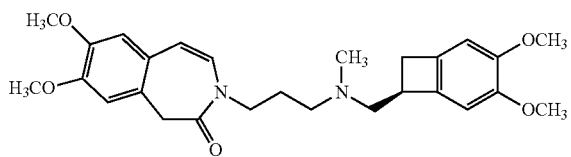

b. treating ivabradine with a solution of an organic acid in an organic solvent to obtain an ivabradine acid addition salt;
 c. optionally purifying the ivabradine acid addition salt;
 d. hydrolysing the ivabradine acid addition salt with a base to produce ivabradine;
 e. treating the ivabradine produced in step d) in situ with alcoholic hydrogen chloride in organic solvent; and
 f. isolating amorphous ivabradine hydrochloride therefrom.

8. The process according to claim 7, wherein in step b), said organic acid is selected from the group consisting of acetic acid, propionic acid, maleic acid, fumaric acid, tartaric acid, oxalic acid, citric acid, benzoic acid, methanesulphonic acid, isethionic acid, benzenesulphonic acid and toluene sulphonic acid.

9. The process according to claim 7, wherein in step b), said organic solvent is selected from the group consisting of lower aliphatic ketones, esters, and nitriles.

10. The process according to claim 7, wherein in step d), said base is selected from the group consisting of sodium hydroxide, potassium hydroxide, sodium carbonate, potassium carbonate, sodium bicarbonate and potassium bicarbonate.

11. The process according to claim 7, wherein in step e), said alcoholic hydrogen chloride contains a $C_1$-$C_4$ branched or linear aliphatic alcohol.

12. The process according to claim 7, wherein in step e), the solvent is selected from the group consisting of methylene dichloride, ethylene dichloride, carbon tetrachloride, chloroform, ethyl acetate, methyl acetate and acetone.

13. A process for the preparation of amorphous ivabradine hydrochloride comprising the steps of:
 a. treating ivabradine with a solution of organic acid in an organic solvent to get an ivabradine acid addition salt;
 b. optionally purifying the ivabradine acid addition salt;
 c. hydrolyzing the ivabradine acid addition salt with a base to produce ivabradine;
 d. treating the ivabradine produced in step d) with alcoholic hydrogen chloride in an organic solvent; and
 e. isolating amorphous ivabradine hydrochloride.

14. The process according to claim 13, wherein in step a), the organic acid is selected from the group consisting of acetic acid, propionic acid, maleic acid, fumaric acid, tartaric acid, oxalic acid, citric acid, benzoic acid, methanesulphonic acid, isethionic acid, benzenesulphonic acid and toluene sulphonic acid.

15. The process according to claim 13, wherein in step a), the organic solvent is selected from the group consisting of lower aliphatic ketones, esters, and nitriles.

16. The process according to claim 13, wherein in step b), the solvent is acetonitrile.

17. The process according to claim 13, wherein in step c), the base is selected from the group consisting of sodium hydroxide, potassium hydroxide, sodium carbonate, potassium carbonate, sodium bicarbonate and potassium bicarbonate.

18. The process according to claim 13, wherein in step d), said alcoholic hydrogen chloride contains a $C_1$-$C_4$ branched or linear aliphatic alcohol.

19. The process according to claim 13, wherein in step d), the organic solvent is selected from the group consisting of methylene dichloride, ethylene dichloride, carbon tetrachloride, chloroform, ethyl acetate, methyl acetate and acetone.

20. A process for the preparation of amorphous ivabradine hydrochloride comprising the steps of:
 a. dissolving ivabradine hydrochloride in a solvent mixture of lower alkanol and ketone at ambient temperature;
 b. heating the solution to 40-50° C.;
 c. distilling out the solvent mixture; and
 d. isolating amorphous ivabradine hydrochloride.

21. The process according to claim 20, wherein said lower alkanol is selected from the group consisting of methanol, ethanol, propanol, and isopropanol; and
 said ketone is selected from the group consisting of acetone, methyl ethyl ketone and methyl isobutyl ketone.

22. A process for the preparation of amorphous ivabradine hydrochloride comprising the steps of:
 a. treating ivabradine hydrochloride with a base in an organic solvent to produce ivabradine, and
 b. treating the ivabradine with alcoholic hydrogen chloride in an organic solvent.

23. The process according to claim 22, wherein in step a), the solvent is selected from the group consisting of ethyl acetate, isopropyl acetate, methyl isobutyl ketone and acetone.

24. The process according to claim 22, wherein in step a), the base is selected from the group consisting of sodium hydroxide, potassium hydroxide, sodium carbonate, potassium carbonate, sodium bicarbonate and potassium bicarbonate.

25. The process according to claim 22, wherein in step b), the alcoholic hydrogen chloride is isopropanolic hydrogen chloride.

26. The process according to claim 22, wherein in step b), the organic solvent is selected from the group consisting of halogenated hydrocarbons and aliphatic esters.

27. A process for the conversion of amorphous ivabradine hydrochloride to a crystalline form of ivabradine hydrochloride comprising the steps of:
 a. heating amorphous ivabradine hydrochloride in an organic solvent;
 b. distilling off some of the organic solvent;
 c. optionally repeating the steps a) and b); and
 d. isolating the α crystalline form of ivabradine hydrochloride.

28. The process according to claim 27, wherein the organic solvent is selected from the group consisting of methyl isobutyl ketone, acetone, ethyl acetate and isopropyl acetate, tetrahydrofuran, isopropyl ether and acetonitrile.

29. Amorphous ivabradine hydrochloride.

30. Crystalline ivabradine oxalate characterized by at least one of the following:
   a. powder X-ray diffraction peaks at about 2.04, 2.13, 4.26, 7.06, 8.02, 8.53, 9.32, 10.91, 13.63, 15.07, 16.11, 16.44, 17.48, 18.37, 19.32, 20.38, 20.94, 21.95, 23.61, 24.26, 27.54 and 33.07 degrees 2θ; or
   b. differential scanning calorimetry thermogram, which shows one endothermic peak around 110° C.

31. The process according to claim 6, wherein in step c), said organic solvent is selected from the group consisting of methylene dichloride, ethylene dichloride, carbon tetrachloride, chloroform, ethyl acetate and methyl acetate.

32. The process according to claim 22, wherein in step b), the organic solvent is selected from the group consisting of methylene dichloride, ethylene dichloride, carbon tetrachloride, chloroform, ethyl acetate and methyl acetate.

* * * * *